(12) United States Patent
Wu et al.

(10) Patent No.: US 7,438,933 B2
(45) Date of Patent: Oct. 21, 2008

(54) MATERNAL MULTI-NUTRIENT AGAINST DIABETES-RELATED BIRTH DEFECTS

(75) Inventors: YingKing Wu, Little Rock, AR (US); E. Albert Reece, Maumelle, AR (US)

(73) Assignee: The Board of Trustees of the University of Arkansas System, Little Rock, AR (US)

( * ) Notice: Subject to any disclaimer, the term of this patent is extended or adjusted under 35 U.S.C. 154(b) by 21 days.

(21) Appl. No.: 11/299,031

(22) Filed: Dec. 9, 2005

(65) Prior Publication Data

US 2006/0128714 A1    Jun. 15, 2006

Related U.S. Application Data

(60) Provisional application No. 60/634,656, filed on Dec. 9, 2004.

(51) Int. Cl.
*A01N 65/00* (2006.01)
*A01N 43/60* (2006.01)
*A61K 36/00* (2006.01)
*A61K 31/525* (2006.01)

(52) U.S. Cl. ..................... 424/725; 514/251

(58) Field of Classification Search .......... 424/725; 514/251

See application file for complete search history.

(56) References Cited

U.S. PATENT DOCUMENTS 6,852,760 B1 * 2/2005 Fine et al. ............ 514/593

OTHER PUBLICATIONS

Reece, E. A.; Wu, Y. "Prevention of diabetic embryopathy in offspring of diabetic rats with use of a cocktail of deficient substrates and an antioxidant" Apr. 1997, Am. J. Obstet. Gynecol., vol. 176(4), pp. 790-798/.*

* cited by examiner

*Primary Examiner*—Sreeni Padmanabhan
*Assistant Examiner*—Kendra D Carter
(74) *Attorney, Agent, or Firm*—Benjamin Aaron Adler

(57) ABSTRACT

The present invention provides uses of multi-nutrient supplements to rescue aberrant biochemical pathways and reduce birth defect caused by maternal diabetes. Choice of supplements is based on the ability of each supplement to correct the following hyperglycemia-associated abnormalities: increased reactive oxygen species generation, abnormal membrane phospholipid metabolism, and decreased glutathione synthesis.

14 Claims, 10 Drawing Sheets

 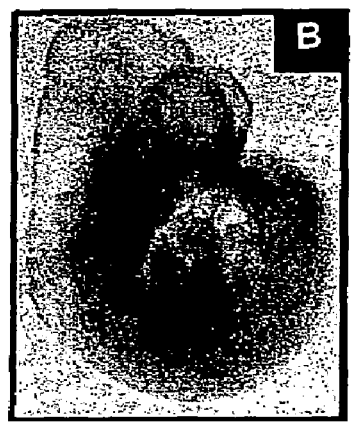 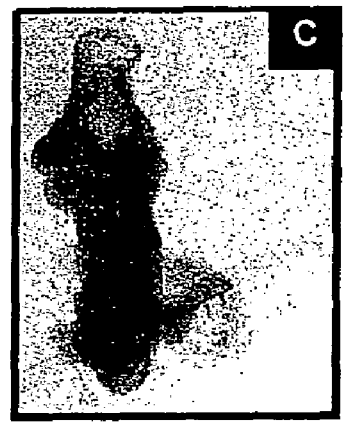
Fig. 1A    Fig. 1B    Fig. 1C
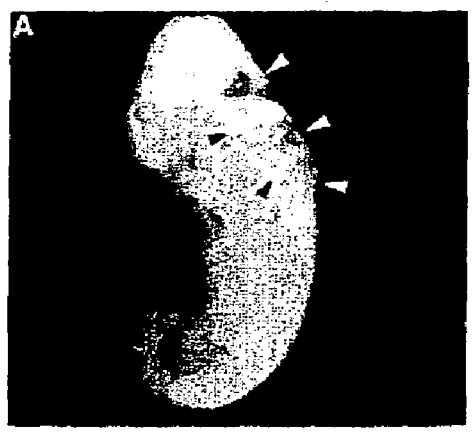 
Fig. 2A    Fig. 2B 1 2 3 4 5
AB AA VE CT NC

AB AA VE CT NC

AB AA VE CT NC

AB AA VE CT NC

MATERNAL MULTI-NUTRIENT AGAINST DIABETES-RELATED BIRTH DEFECTS

CROSS-REFERENCE TO RELATED APPLICATION

This non-provisional application claims benefit of provisional U.S. Ser. No. 60/634,656, filed Dec. 9, 2004, now abandoned.

BACKGROUND OF THE INVENTION

1. Field of the Invention

The present invention relates generally to the study of congenital malformation. More specifically, the present invention relates to methods of preventing diabetes-related congenital malformation.

2. Description of the Related Art

Each year in the United States, about 150,000 babies—3% of all live births are born with a major congenital malformation. This problem is worse in offspring of women who have type 1 or 2 diabetes; 6%-10% of these babies are born with a major congenital malformation. Based on the National Health and Nutrition Examination Survey conducted during 1988-1994, 1.1% of women 20-39 years of age have type 1 or 2 diabetes, and the incidence of diabetes among women of childbearing age has been increasing over the past four decades. It is projected that the number of women of childbearing age with type 2 diabetes will double by 2010, suggesting that approximately 8,000 babies will be born each year in the United States with a congenital malformation secondary to type 1 or 2 diabetes.

Human observational studies have demonstrated a strong link between the extent of a mother's glycemic control and the incidence of congenital malformations in her offspring. The putative teratogenic effects of hyperglycemia are supported by studies that demonstrate a reduction in the incidence of birth defects following clinical intervention targeted at achieving euglycemia. When euglycemia is successfully maintained periconceptionally and during the first trimester, the prevalence of malformations is reduced to a level comparable to that of the general population. However, even with excellent compliance and clinical care, euglycemia may be difficult to achieve and maintain. In addition, it is possible that organogenesis can be affected by short periods of hyperglycemia that are not reflected in the averaged values of glycosylated hemoglobin levels, which are used to monitor glucose levels. A further obstacle is that most women with diabetes do not seek preconceptional care and most have unplanned pregnancies. Hence, a very important goal for public health is to develop and implement accessible intervention strategies to diminish the occurrence of these anomalies.

Both clinical cases and animal studies have clearly demonstrated that the main characteristics of maternal hyperglycemia-associated defects are organogenesis and underdevelopment. The organ systems most commonly affected include the central nervous, cardiovascular, gastrointestinal, craniofacial, genitourinary, and skeletal systems. Because the neural folds and heart develop early during embryogenesis, a higher incidence of malformations is often seen in these organs. In the central nervous system, abnormalities can be categorized as underdevelopment of the midbrain and hindbrain and failure of the neural tube to close at both anterior (rostral) and posterior (caudal) ends of the neural axis. The failure of posterior neural tube closure results in spina bifida, a common birth defect seen in newborns.

Convincing evidence from clinical and experimental studies demonstrates that diabetes-related hyperglycemia leads to sustained generation of reactive oxygen species (ROS) and depletion of antioxidant defense, resulting in intracellular oxidative stress due to an imbalance in intracellular reduction-oxidation (redox) homeostasis. Under normal physiological conditions, oxygen free radicals, including hydroxyl radicals, superoxide anions, singlet oxygen, and hydrogen peroxide ($H_2O_2$), are produced during cellular energy metabolism in sub cellular organelles such as mitochondria. The reactive oxygen species mediate intracellular signal transduction that regulates a wide range of cell functions, including proliferation, differentiation, and migration. However, under pathological conditions, excess reactive oxygen species can oxidize proteins, lipids, and DNA, causing cell injury and even cell death.

Over the past two decades, multiple clinical and experimental studies have evaluated the efficacy of maternal dietary supplements to decrease the rate of diabetic embryopathy. Supplements that potentially alter the underlying hyperglycemia-induced increases in oxidative stress, decreases in antioxidant defense, and alterations in membrane lipid metabolism are most relevant.

Lipoic acid and vitamin C reduce reactive oxygen species-mediated effects and support generation of other antioxidants. Lipoic acid is a naturally occurring antioxidant that is an effective scavenger of free radicals. In experimental models, lipoic acid has been shown to reduce malformation rate in diabetic pregnancies from 25% to 10%. In clinical studies of non-pregnant diabetic individuals, lipoic acid lowered the plasma lipid hydroperoxides, demonstrating a decrease in oxidative stress. This effect was maintained even in patients with high glucose levels. Vitamin C is a hydrophilic molecule that can scavenge several free radicals, including the hydroxyl radical. Experimental studies have demonstrated that vitamin C supplementation reduces the rate of embryonic malformations and embryo resorption.

Dietary supplements containing arachidonic acid (AA) and vitamin E prevent membrane lipid peroxidation and may be beneficial for primary prevention of diabetic embryopathy. In vitro and in vivo experimental studies demonstrated that maternal supplementation with arachidonic acid reduced hyperglycemia-induced aberrant membrane lipid metabolism, suggesting a protective effect. Vitamin E is a major lipid-soluble antioxidant that protects biological membranes from lipid peroxidation. Following a diet supplemented with vitamin E, pregnant diabetic rats have higher serum vitamin E levels and lower embryonic malformation and resorption rates than non-supplemented diabetic rats.

Both N-acetylcysteine (NAC), a cysteine progenitor, and folic acid, a methionine/cysteine precursor, increase glutathione synthesis. In experimental models, supplementation with N-acetylcysteine reduced development of peripheral neuropathy and embryopathy in diabetic rats. This may be due to increase in glutathione synthesis and antioxidant capacity in the cell. It is well accepted that dietary supplementation with folic acid prevents neural tube defects in both experimental and clinical models. In diabetic rats, folic acid levels are especially low in the heart, brain, kidney, and muscle.

For each supplement discussed, lipoic acid, vitamin C, arachidonic acid, vitamin E, N-acetylcysteine, and folic acid, animal and human studies have demonstrated that each nutrient is lower among diabetic individuals than non-diabetic individuals. Clinical trials among diabetic patients have demonstrated that a reduction in diabetic complications (i.e., glycemic control, neuropathy, nephropathy, retinopathy, vasculopathy) may occur following supplementation with these compounds. Most of the published studies, however, focused on the effects of a single nutrient, and no randomized clinical trials evaluating adjunctive therapy with antioxidants to prevent diabetic embryopathy have been published.

Thus, it is desirable to define an optimal intervention strategy of using combinations of nutrients for primary prevention of maternal hyperglycemia and diabetic embryopathy. The present invention fulfills this long-standing need and desire in the art.

SUMMARY OF THE INVENTION

In one embodiment, there are provided a dietary supplement and a method of using such supplement to reduce birth defect caused by maternal diabetes. The dietary supplement comprises lipoic acid, vitamin C, vitamin E, arachidonic acid, folic acid, and glutathione precursor N-acetylcysteine.

In another embodiment, there are provided a dietary supplement and a method of using such supplement to reduce birth defect caused by maternal diabetes. The dietary supplement comprises one or more antioxidants, one or more compounds that improve membrane lipid metabolism (e.g. arachidonic acid), and one or more compounds that support glutathione synthesis (e.g. methionine/cysteine precursor and glutathione precursor).

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIGS. 1A-C are photographs of rat embryos on embryonic day 12. FIG. 1A: C-shaped form of a normal embryo from a non-diabetic rat. FIG. 1B: malformed embryo from a diabetic rat with an open neural tube defect. FIG. 1C: dorsal view of a malformed embryo.

FIGS. 2A-B show exposure of conceptus to serum medium containing 950 mg/dl D-glucose. FIG. 2A: Rat embryo with neural tube defect, outlined by arrows. FIG. 2B: Rat embryo with heart defect (1), pericardial effusion (2), neural tube defect (3), and dorsal tail flexion (4).

FIG. 4A: Western blot detection of Caspase3 (casp3) and Bax using antibodies against phosphorylated proteins. Lane 1: malformed embryos of diabetic dams without supplementation; lane 2: embryos of diabetic dams supplemented with arachidonic acid; lane 3: embryos of diabetic dams supplemented with vitamin E; lane 4: embryos of diabetic dams supplemented with a combination of arachidonic acid, vitamin E and myoinositol; lane 5: normal embryos of non-diabetic dams without supplementation. Densitometrical analysis of changes in casp3 (FIG. 4B) and Bax (FIG. 4C). NC, non diabetic control; AB, abnormal embryo of diabetic dam; ND, normal embryo of diabetic; AA, supplemented with arachidonic acid; VE, supplemented with vitamin E; and CT, supplemented with a combination of arachidonic acid, vitamin E and myoinositol

FIG. 6A shows Western blot detection of ERK1/2, JNK1/2 Raf-1 and Akt using antibodies against phosphorylated forms of these proteins. Densitometrical analysis of changes of ERK1/2, JNK1/2 Raf-1 and Akt are shown in FIGS. 6B 6C, 6D and 6E respectively. NC, non diabetic control; AB, abnormal embryo of diabetic; ND, normal embryo of diabetic.

DETAILED DESCRIPTION OF THE INVENTION

Birth defects caused by maternal diabetes are a major health problem. It has been suggested that embryonic malformation is associated with oxidative stress, which induces excessive cell death in embryo and yolk sac. A number of factors, such as PKC, $cPLA_2$, and MAPKs have been implicated in diabetic embryopathy. However, the roles of these factors in embryonic malformation and the mechanisms by which these factors regulate reactive oxygen species production and apoptosis are largely unknown.

Results presented herein indicate that exposure to maternal hyperglycemia induces both an increase in oxidative stress and a decrease in glutathione-mediated antioxidant defense in developing embryos. This in turn causes aberrations in stress-activated MAPK signaling pathways and membrane phospholipids signal transduction pathways, and result in excessive apoptosis and dysmorphogenesis. In addition, there is biochemical deficiencies in membrane lipids (arachidonic acid and myoinositol) and excess reactive oxygen species.

These findings suggest that hyperglycemia activates PKC in the cell. Activated PKC activates $cPLA_2$, leading to lipid peroxidation and increased production of reactive oxygen species. Elevated oxidative stress alters MAPK activation, possibly by increasing JNK activity. Increased JNK activity promotes release of cytochrome C from mitochondria, which activates caspase 9 and caspase 3, leading to apoptosis. The roles and mechanisms of these factors and signaling pathways in diabetic embryopathy can be examined using an in vivo maternal diabetic animal model and in vitro whole embryo and cell cultures combined with contemporary cellular and molecular biological techniques. Data obtained from these experiments will provide important information for developing therapeutic approaches to prevent birth defects.

Figure 9:
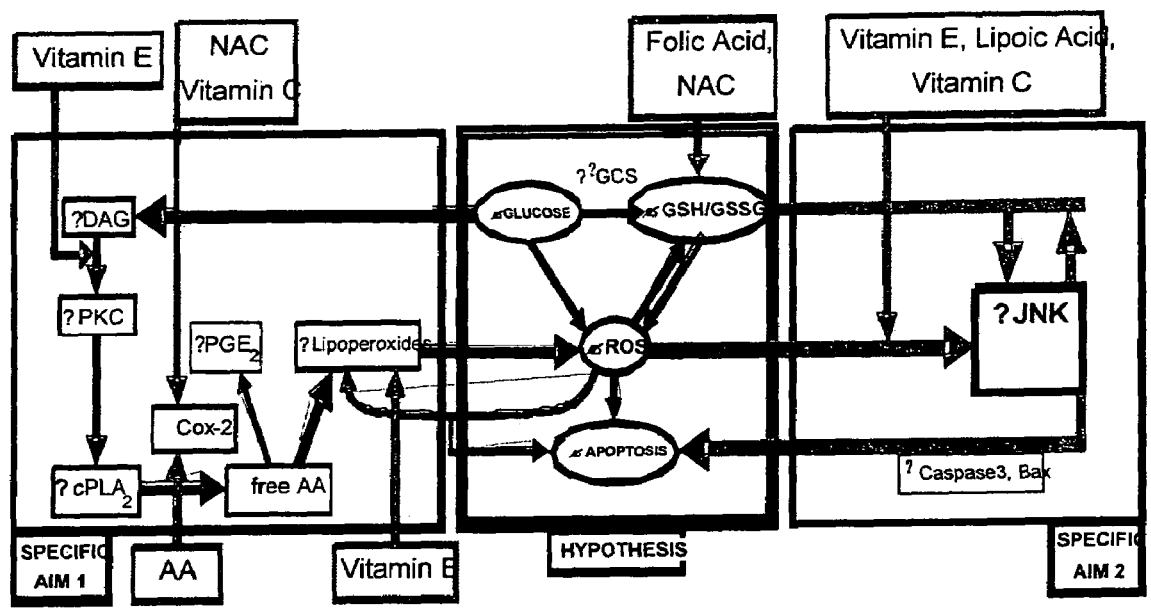
FIG. 9 depicts a diagram of targeted intervention strategy to counteract hyperglycemia-induced alterations involved in diabetic embryopathy. Each of the nutritional supplements has been selected based on its ability to reduce diabetic malformations and to normalize specific pathways known to be adversely affected by hyperglycemia. The point of interaction for each supplement is indicated by a purple box.

It is hypothesized that nutritional supplements, especially antioxidants, can inhibit and/or reduce the rates of apoptosis and malformation in embryos under hyperglycemic conditions. Choice of supplements is based on the ability of each supplement to correct the following hyperglycemia-associated abnormalities: increased reactive oxygen species generation, abnormal membrane phospholipid metabolism, and decreased glutathione synthesis (FIG. 9).

For example, three sets of supplements are selected to correct three different levels of hyperglycemia-induced aberrations that contribute to diabetic embryopathy. The first supplement set is a combination of two potent antioxidants, lipoic acid and vitamin C, and is designed to reduce reactive oxygen species-mediated effects and to support reductive regeneration of other antioxidants. Lipoic acid and its reduced form, dihydrolipoic acid, are thiol antioxidants that are soluble in both aqueous and membrane compartments and function as scavengers of hydroxyl radicals and singlet oxygen in membranes and cytosol. Lipoic acid has been shown to decrease oxidative stress in diabetic patients with poor glycemic control, and to reduce malformations in embryos of STZ-induced diabetic rats. Vitamin C is a potent scavenger of several reactive oxygen species including hydroxyl radical, singlet oxygen, and superoxide radical, and it intervenes to inhibit membrane lipid peroxidation. Both lipoic acid and vitamin C interact with other antioxidants to provide reducing equivalents for the regeneration of active vitamin E and GSH. Therefore, it is predicted this combination of antioxidants will increase total antioxidant capacity in diabetic mothers despite their ongoing hyperglycemia.

The second supplement set is a combination of vitamin E and arachidonic acid, and is designed to prevent membrane lipid peroxidation and improve aberrant membrane lipid metabolism associated with hyperglycemia. Vitamin E is a major lipid-soluble membrane antioxidant that acts as a peroxidation chain-breaking agent to prevent loss of membrane function and integrity. Vitamin E supplementation of children with type 1 diabetes reduced erythrocyte lipid peroxidation. It has been shown that supplementing the diets of diabetic rats with arachidonic acid reduces malformation rates in vitro and in vivo. By combining vitamin E and arachidonic acid supplementation, it is anticipated that an interactive effect on membrane structure and function will reduce malformation rates to a greater extent than either alone.

The third supplement set combines glutathione precursor N-acetylcysteine (NAC), with the methionine/cysteine precursor folic acid and is designed to support and augment glutathione synthesis in diabetic mothers. Analysis of intracellular metabolites in the glutathione pathway indicated that malformed embryos and yolk sacs were severely depleted of glutathione (GSH) antioxidant capacity (2-4-fold reduction in GSH/GSSG). Results presented above indicated a decrease in methionine and an increase in homocysteine, consistent with a deficiency in functional folate induced by chronic oxidative stress and an increased requirement for glutathione. The increase in cysteine in malformed embryos and yolk sacs strongly supports the hypothesis that γ-glutamylcysteine synthetase expression and activity are reduced during hyperglycemia-induced oxidative stress. It is expected that supplementation with folic acid will increase methionine, decrease homocysteine, and increase GSH synthesis in diabetic mothers.

Individual supplement sets may reduce, but not completely prevent, malformations and that a combination of two or more supplement sets may reduce malformation rates to background levels in diabetic mothers. Identification of metabolic and molecular endpoints that are significantly shifted by supplementation toward the levels in normal embryos and yolk sacs will provide strong evidence to suggest that these alterations are the most significant in the genesis of diabetic embryopathy. The comparison of the magnitude of these changes between embryos and yolk sacs is expected to provide important insights into the relative importance of each in the development and prevention of malformations.

In one embodiment, the present invention provides a dietary supplement and a method of using such supplement to reduce birth defect caused by maternal diabetes. The dietary supplement comprises (a) an effective amount of a source of lipoic acid; (b) an effective amount of a source of vitamin C; (c) an effective amount of a source of vitamin E; (d) an effective amount of a source of arachidonic acid; (e) an effective amount of a source of folic acid; and (f) an effective amount of a source of glutathione precursor N-acetylcysteine.

It is known that myoinositol when administered in combination with vitamin E and arachidonic acid reduces embryonic defect rate in diabetes related pregnancy. It is also speculated that under hyperglycemic conditions there is a widespread relative intracellular myoinositol deficiency in man, which suggests that restoration of normal intracellular myoinositol concentrations might prove to benefit in the prevention and treatment of certain complications because of diabetes. Accordingly it is contemplated that an effective amount of myoinositol may be added in the instant dietary supplement to reduce birth defect caused by maternal diabetes.

Preferably, the effective amount of lipoic acid is from about 1 mg to about 100 mg per day; more preferably, the effective amount of lipoic acid is from about 5 mg to about 20 mg per day. The effective amount of vitamin C is from about 10 mg to about 500 mg per day; more preferably, the effective amount of vitamin C is from about 75 mg to about 150 mg per day. The effective amount of vitamin E is from about 50 IU to about 500 IU per day; more preferably, the effective amount of vitamin E is from about 200 IU to about 300 IU per day. The effective amount of Safflower oil, the source of arachidonic acid that comprises at least 79% of linoleic acid, is 1-100 ml daily; more preferably 5-10 ml daily. The effective amount of N-acetylcysteine is from about 50 mg to about 750 mg three times a day; more preferably, the effective amount of N-acetylcysteine is from about 250 mg-500 mg three times a day. The effective amount of and the effective amount of [6S]-5-methyltetrahydrofolate (MTHF), one of the derivative folic acid, is from about 100 μg to about 800 μg per day.

In general, the dietary supplement is administered to an individual before or during pregnancy. The supplement can be administered by a suitable means of consumption generally known and practiced in the art. For example, the supplement can be taken as a tablet or capsule which can be easily swallowed, chewed, or dissolved. Alternatively, the dietary supplement can be formulated into a powder or liquid for convenient addition to drinks, baked goods, dairy products or other food stuffs. The dietary supplement can also be consumed in the form of a snack bar, drink or lozenge. The supplement preferably is consumed on a daily basis, e.g., once a day. The dietary supplement can also be consumed multiple (greater than one) times a day.

In another embodiment, there are provided a dietary supplement and a method of using such supplement to reduce birth defect caused by maternal diabetes. The dietary supplement comprises one or more antioxidants, one or more compounds that improve membrane lipid metabolism, and one or more compounds that support glutathione synthesis. In general, the antioxidants can be vitamin C, vitamin E and lipoic acid. Examples of compounds that improve membrane lipid metabolism include arachidonic acid, and compounds that support glutathione synthesis include methionine/cysteine precursor (e.g. folic acid) and glutathione precursor (e.g. N-acetylcysteine). This supplement may further contain an effective amount of myoinositol. These various nutrients can be formulated and administrated as that described above.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Maternal Diabetic Model

In order to study maternal diabetes-associated embryopathy, an animal model has been generated in which streptozotocin (STZ) is used to induce diabetes in female rats. Their glucose levels are controlled by reintroducing insulin in the form of a removable, implanted pellet. This type of animal model, which has been widely used, has a number of advantages over spontaneous diabetic animal models. First, glucose levels can be controlled by changing the amount of insulin introduced. Second, diabetes can be induced at desired developmental stages by removing the insulin pellet at appropriate time. Similar mouse models have also been used by other researchers in this field with similar reported outcomes.

To induce diabetes, 8-week-old Sprague-Dawley female rats are injected with 65 mg/kg of streptozotocin via the tail vein. Blood glucose levels are monitored daily (by tail vein puncture using a lancet) using a Prestige Smart blood glucose meter (Home Diagnostics, Fort Lauderdale, Fla.). Once a level of hyperglycemia indicative of diabetes (>250 mg/dl) is achieved, a sustained-release insulin pellet (Linplant, Linshin, Canada) will be inserted subcutaneously.

When glucose levels are restored to normal (80-150 mg/dl) and are stable for at least three continuous days, matings can be set up with male rats of the same strain. Day zero of pregnancy is established by identifying spermatozoa in vaginal smears. At designated developmental stages, insulin pellets are withdrawn to generate hyperglycemia in the pregnant rats. A group of control rats will continuously receive insulin during the course of the experiment. Glucose levels and maternal weight are continuously monitored during the pregnancy. Since it has already been shown that there is no difference in embryonic development between streptozotocin/insulin-treated and non-streptozotocin-treated animals, the streptozotocin/insulin-treated groups are used as an equivalent of non-diabetic control. At the end of the experiment, rats are euthanized and embryos dissected out of the uterus for examination and analysis. At least four pregnant rats are included in each group, from which 40-60 embryos can be obtained for examination. For each type of study, at least three replicate experiments will be carried out.

The embryos are characterized morphologically in terms of growth and structural abnormality. Embryonic growth can be determined by the size of embryo, including head/rump length and body weight. Structural abnormality includes agenesis, hypoplasia, incomplete neural tube closure, microcephaly, cardiac defects, and incorrect body curvature. Specimens are also sectioned and examined at the histological level. Special attention will be paid to the organs that have been documented to be negatively affected by hyperglycemia.

Whole Embryo Culture

While the in vivo diabetic animal model provides important information about morphological and molecular changes during development, it is difficult to treat the embryos in utero with drugs. To delineate the roles of factors in hyperglycemia-associated embryonic malformation, a whole embryo culture system can be used in which the embryos are exposed to different glucose concentrations. It has been validated that this type of whole embryo culture mimics in vivo development of embryos under maternal diabetes. In this culture system, the embryos are treated with drugs that disturb the activity of specific factors and components of signaling pathways. A whole-embryo culture system, modified from the roller bottle system, has been routinely used. This culture system allows embryos from stages E8.5 to E12.5 to develop normally in vitro for 48-72 hours with controlled $O_2$ levels that mimic conditions in utero. Therefore, it is a useful, reliable, and manipulable system for studying early embryogenesis and organogenesis.

Embryos at different stages of gestation can be dissected out of uterus with the yolk sacs intact. The embryos are then cultured in rat serum (five embryos/bottle) at 38° C. with rotation at 30 revolutions per minute. Glucose are added to the cultures to generate euglycemic (80-150 mg/dl) and various hyperglycemic (300 mg/dl, 600 mg/dl, 950 mg/dl) conditions. Embryos are treated with drugs under hyperglycemic and control conditions for 24-72 hours. At the end of culture, embryos are collected for morphological and histological examination and biochemical analyses. At least 10 embryos are included in each group. Each type of experiment can be done in triplicate.

Cell Culture

The maternal diabetic animal model and embryo culture described above provide useful systems for investigating the effects of hyperglycemia on embryogenesis and the mechanisms by which hyperglycemia causes developmental malformations. To delineate the molecular mechanisms in depth, a cell culture systems can be used to test various hypotheses at cellular and molecular levels.

For example, NIH 3T3 fibroblasts, which are derived from murine embryonic cells, are suitable for delineating the molecular mechanisms of hyperglycemia-induced embryopathy. 3T3 cells can be purchased from American Type Culture Collection (ATCC, Manassas, Va.) and maintained in conditions recommended by ATCC. For each experiment, cells are plated and grown to desired density before treatment. After treatment, cells are harvested at different time points for cellular and molecular analyses. Primary embryonic cells from the tissues affected by hyperglycemia can also be examined to investigate if there are cell type-specific effects.

EXAMPLE 2

Maternal Diabetes Correlates with Increased Embryo Malformation Rates

To investigate the effects of maternal hyperglycemia on embryonic malformations, the investigators employed a rat model that induces diabetes by streptozotocin (STZ). Subcutaneously implanted insulin pellets maintained euglycemia at the time of mating. On day 4 of pregnancy, the insulin pellets were removed, and the developing embryos were exposed to hyperglycemia during organogenesis (days 9-12). To maintain a euglycemic control, insulin pellets were retained in the body during the entire experimental course. On day 12, both sets of rats were euthanized, embryos were dissected out of the uteri for examination, and each embryo's yolk sac was collected for biochemical and molecular analyses.

After removal from the dams, embryos were examined under a dissecting microscope and assessed for morphological malformations in a number of categories to determine the effects of maternal hyperglycemia. Embryos were classified as normal if examination revealed correct body flexure, both anterior and posterior neural pole closure, and grossly normal heart (FIG. 1A). Embryos were classified as malformed if they showed evidence of neural tube defects (NTDs; FIGS. 1B and C) or other malformations, including cardiac abnormalities, incorrect body curvature, reverse tail flexion, and microcephaly. The results demonstrate that malformation rates (as assessed by morphological defects) in the diabetic rats are more than 6-fold higher than that in non-diabetic control rats or in euglycemic control rats whose insulin pellets were left in place (Table 1). Furthermore, these data suggest that increased malformation rates are due to maternal diabetes per se, rather than STZ treatment.

TABLE 1

Average Glucose Levels And Rates of Neural Tube Defects (NTDs) In Embryos of Non-Diabetic And Diabetic Rats

| Experimental groups | Embryos (n) | Average glucose level* (mg/dl) | Embryos with NTDs/total embryos (%) |
|---|---|---|---|
| Non-diabetic (control) | 191 | 109 ± 8.1 | 1.6 ± 0.9 |
| Diabetic + insulin pellet (STZ control) | 58 | 164 ± 33.1 | 1.7 ± 1.7 |
| Diabetic + insulin pellet + removal (experimental) | 158 | 305 ± 35.4 | 12.7 ± 2.7 |

*Average glucose level is the mean of glucose levels on gestational days 4-12.

EXAMPLE 3

Hyperglycemia Induces Embryonic Malformations In Vitro

To further test whether hyperglycemia plays a role in increased malformation rates in the embryos, an in vitro embryo culture model was used in which experimental conditions can be precisely controlled. Embryos at E10 were cultured in control medium consisting of 80% (vol/vol) rat serum in which glucose concentration was 150 mg/dl. Embryos were treated with various concentrations of glucose. After 24 hours of culture, control embryos developed normally into E11-like embryos. However, embryos treated with high concentrations of glucose (300 mg/dl, 600 mg/dl, and 950 mg/dl) exhibited abnormalities of the neural tube, heart, pericardium, and body flexion (FIG. 2). These phenotypes are similar to those seen in in vivo maternal diabetes experiments, indicating that hyperglycemia directly affects embryonic development in vitro in a manner corresponds to that seen in vivo. These experiments demonstrate that high concentrations of glucose have teratogenic effects on embryos, and whole embryo culture provides a powerful experimental system to test various aspects of hyperglycemic effects on embryonic development.

EXAMPLE 4

Maternal Hyperglycemia Results in Impaired Antioxidant Defense Mechanisms in Embryos To test the hypothesis that hyperglycemia causes oxidative damage to cells by disrupting redox balance between reactive oxygen species generation and antioxidant defense, diabetes was induced in pregnant rats. Embryos' yolk sac tissues were collected and analyzed for levels of antioxidants. High-pressure liquid chromatography (HPLC) with electrochemical detection was used to analyze intracellular levels of oxidized and reduced glutathione and their metabolic precursors, cysteine (reduced), cystine (oxidized), methionine, and homocysteine.

Results shown in Table 2 indicate a significant and nearly twofold decrease in redox ratio (GSH/GSSG) in malformed versus normal embryos. This decrease is primarily due to significant increase in oxidized (inactive) GSSG. In the yolk sac tissues, an almost threefold decrease in GSH/GSSG ratio was observed, indicating a highly significant increase in oxidative stress. Depletion of methionine, the precursor for cysteine/glutathione synthesis, was a further indication of chronic oxidative stress, while an increase in homocysteine and cysteine was consistent with hyperglycemia-induced inhibition of γ-glutamylcysteine synthetase (γ-GCS), the rate-limiting enzyme for glutathione synthesis.

These data provide strong evidence that glutathione-mediated antioxidant defense mechanisms are severely compromised in embryos subjected to maternal hyperglycemia during the critical stages of organogenesis, supporting the hypothesis that maternal hyperglycemia increases oxidative stress and depletes antioxidant capacity.

TABLE 2

Mean Levels of GSH, GSSG, And Their Metabolic Precursors In Embryos And Yolk Sacs From Non-Diabetic And Diabetic Rats (Mean ± SD; μM)

|  | Experimental Groups | N | GSH (reduced) | GSSG (oxidized) | GSH/GSSG (redox ratio) | Methionine | Homo-cysteine | Cysteine (reduced) | Cystine (oxidized) |
|---|---|---|---|---|---|---|---|---|---|
| Embryo | Non-diabetic (normal) | 6 | 11.0 ± 0.9 | 0.5 ± 0.1 | 22.7 ± 4.2 | 6.1 ± 1.0 | 0.2 ± 0.04 | 5.0 ± 0.3 | 10.6 ± 1.3 |
|  | Diabetic (malformed) | 4 | 13.3 ± 0.5* | 1.0 ± 0.2* | 13.6 ± 2.7* | 4.0 ± 0.8* | 0.5 ± 0.1* | 7.2 ± 1.5* | 18.3 ± 3.1* |

TABLE 2-continued

Mean Levels of GSH, GSSG, And Their Metabolic Precursors In Embryos And Yolk Sacs From Non-Diabetic And Diabetic Rats (Mean ± SD; µM)

| | Experimental Groups | N | GSH (reduced) | GSSG (oxidized) | GSH/GSSG (redox ratio) | Methionine | Homo-cysteine | Cysteine (reduced) | Cystine (oxidized) |
|---|---|---|---|---|---|---|---|---|---|
| Yolk sac | Non-diabetic (normal) | 7 | 2.0 ± 0.4 | 0.03 ± .01 | 67.7 ± 26 | 2.1 ± 0.6 | 0.1 ± .04 | 3.6 ± 0.5 | 8.9 ± 2.4 |
| | Diabetic (malformed) | 6 | 1.2 ± 0.2* | 0.07 ± .02* | 17.4 ± 3.2* | 1.4 ± 0.3* | 0.3 ± .07* | 5.1 ± 1.2* | 13.2 ± 2.18* |

*p < 0.05 relative to control

EXAMPLE 5

Maternal Hyperglycemia Causes Apoptosis in the Yolk Sac

It has been suggested that programmed cell death is involved in hyperglycemia-induced embryonic malformations, and deviations in apoptosis may play a major role in this process. Several markers were used to investigate whether hyperglycemia is associated with changes in apoptosis in yolk sacs.

Figure 3:
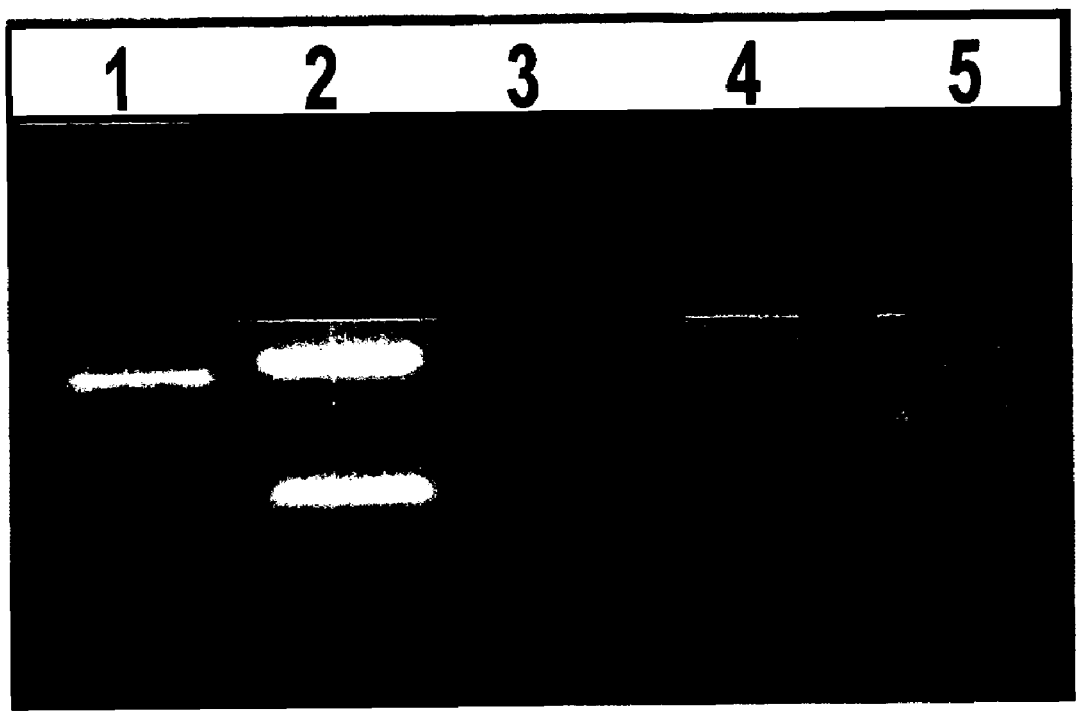
FIG. 3 shows agarose gel electrophoresis assay of DNA laddering in yolk sac cells. Lanes 1 and 2: DNA molecular weight makers; lane 3: normal embryos of non-diabetic dams; lane 4: malformed embryos of diabetic dams; lane 5: normal embryos from diabetic dams.

One of the features of apoptosis is DNA fragmentation, which can be recognized by the characteristic laddering band pattern visualized by agarose gel electrophoresis. To determine whether hyperglycemia is associated with programmed cell death in embryos, DNA laddering was examined in yolk sacs of embryos with either diabetic or non-diabetic mothers. Yolk sac tissues were collected from embryos, and DNA was extracted using DNeasy Tissue Kit (Qiagen, Valencia, Calif.) and resolved on 0.5% agarose gel. FIG. 3 clearly demonstrates the presence of DNA laddering in yolk sac cells of malformed embryos from diabetic rats and the absence of laddering in yolk sac cells of normal embryos from diabetic and non-diabetic rats. These data indicate that apoptosis is increased in the yolk sacs of malformed embryos under maternal diabetic conditions.

Figure 4A:
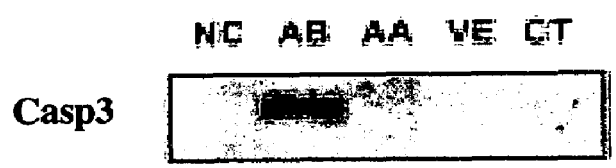
FIGS. 4A-C show Western blot assay of caspase3 and Bax activation in yolk sac cells and the effects of maternal supplementation on the levels of these proteins.
Figure 4A:

Apoptosis is mediated by a program involving a number of factors, including caspase3 and Bax (a member of the Bcl-2 family). Hyperglycemia may stimulate JNK activity, which then activates caspases and leads to apoptosis. Activation of Bax is also a hallmark of ongoing apoptosis. To determine whether caspase and Bax activation are involved in maternal diabetic embryopathy, changes in the levels of phosphorylated caspase3 and Bax in yolk sac cells from embryos with either diabetic or non-diabetic mothers were assessed. Cell lysates were resolved on 12% polyacrylamide gel and blotted on nylon membrane. The blots were probed with antibodies raised against phosphorylated caspase3 or Bax (Santa Cruz Biotechnologies, Santa Cruz, Calif.). Signals were detected using a chemiluminescence detection method and exposed to X-ray film (FIG. 4A).

Figure 4B:
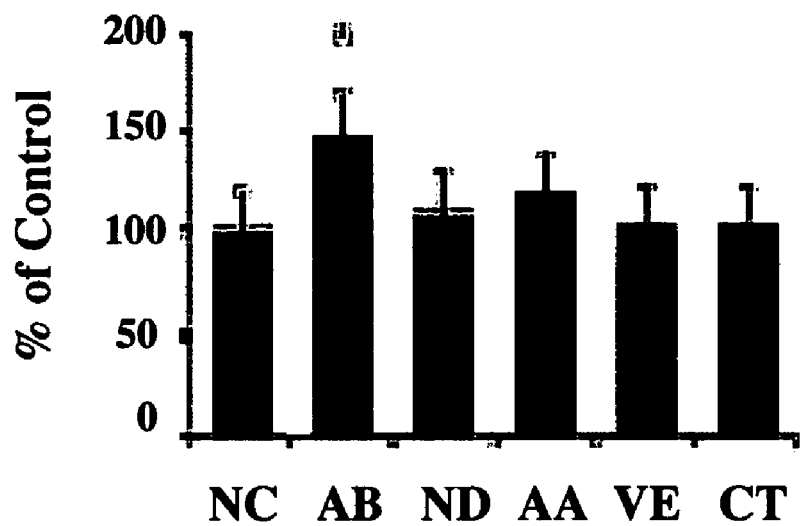
Figure 4C:
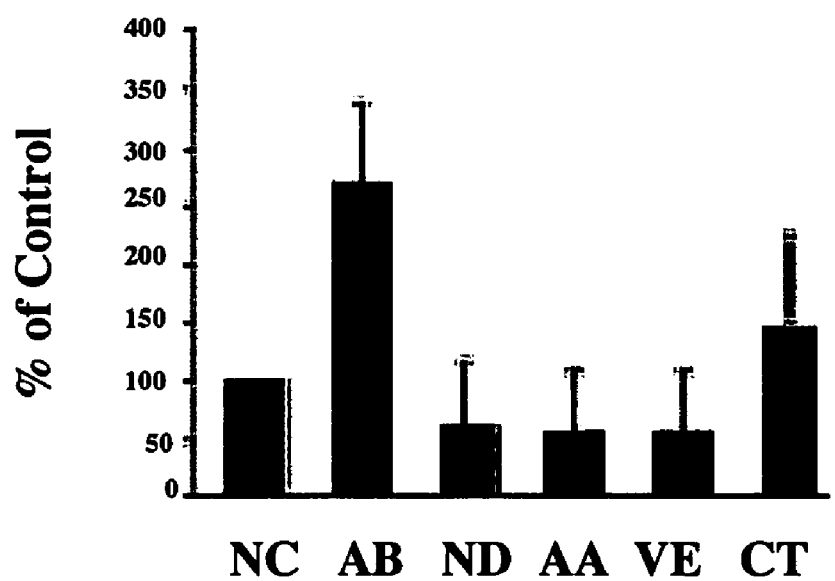

The density of the bands on X-ray film was measured using densitometry (VersaDoc Imaging System, Bio-Rad, Hercules, Calif.) and analyzed with one-dimensional analysis software (Bio-Rad; FIGS. 4B and C). The value of each band was calculated as a percentage of the control, which was set at 100%. It was found that phosphorylated caspase3 and Bax levels were significantly increased in yolk sac cells of malformed embryos from diabetic rats, in comparison with normal embryos from either non-diabetic or diabetic mothers (FIG. 4). These data support the hypothesis that hyperglycemia induces embryonic apoptosis involving caspases. FIG. 4A further illustrates the reversal of increased caspase3 and Bax levels in yolk sacs of malformed embryos from diabetic rats in the presence of arachidonic acid, vitamin E or a combination of arachidonic acid, vitamin E and myoinositol.

EXAMPLE 6

Maternal Hyperglycemia Correlates with Increases in CPLA$_2$ Level in Yolk Sacs

Figure 5A:
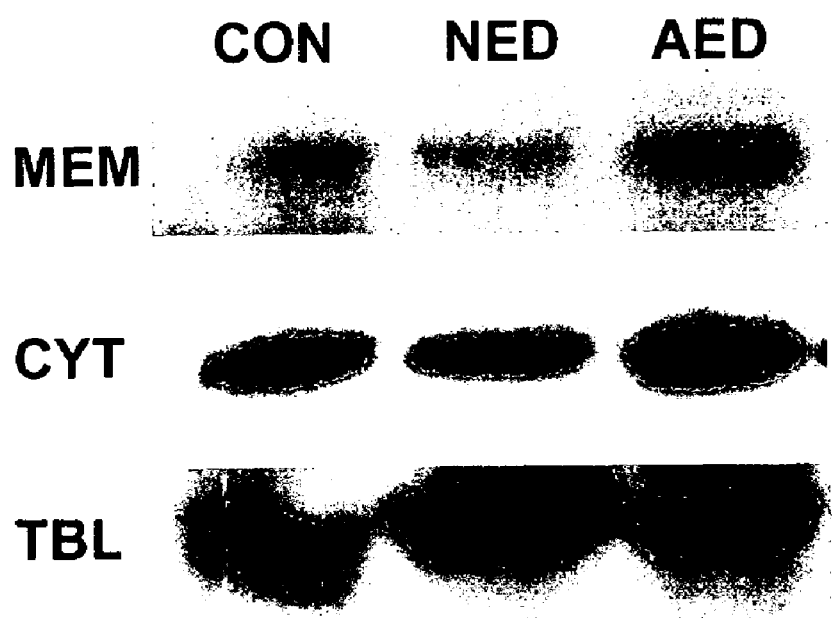
FIGS. 5A-B show Western blot assay of $cPLA_2$ in yolk sacs. Western blots probed with anti-$cPLA_2$ antibody (FIG. 5A), and $cPLA_2$ levels were quantitated using densitometry (FIG. 5B). CON, non-diabetic control; NED, normal embryo of diabetic; AED, abnormal embryo of diabetic; MEM, membrane fraction; CYT, cytosolic fraction; TBL, tubulin (loading control).

Hyperglycemia may increase PKC and cPLA$_2$ activity in cell membranes, triggering lipid peroxidation pathway and ultimately contributing to embryopathy. To address this hypothesis, preliminary experiments was conducted to determine whether cPLA$_2$ activity was increased in malformed embryos from diabetic mothers. Yolk sacs of embryos from diabetic and non-diabetic dams were isolated and used in Western blot analysis to examine changes in cPLA$_2$. Yolk sacs were homogenized and centrifuged to separate cytosolic and membrane fractions. Fractionated cell lysate proteins were resolved on 12% polyacrylamide gel and blotted on a nylon membrane. The blots were probed with antibodies raised against cPLA$_2$ (Santa Cruz Biotechnologies; FIG. 5A). Chemiluminescent signal detection and data analysis were performed as described above.

Figure 5B:
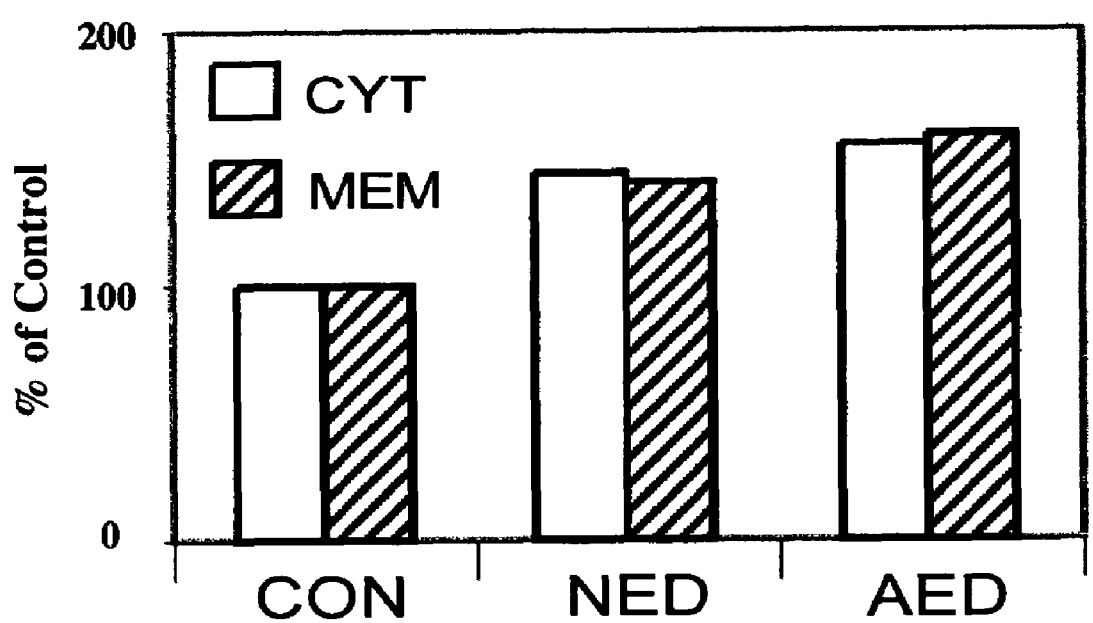

Significant increases in cPLA$_2$ was found in membrane fraction from malformed yolk sacs, as compared with those from normal embryos isolated from non-diabetic dams (FIG. 5B). A moderate increase was seen in normal embryos from diabetic mothers. Similar changes were also observed in the cytosolic fraction. These results suggest that hyperglycemia activates cPLA$_2$, potentially leading to lipid peroxidation. Similar experiments can be performed to further investigate PKC and cPLA$_2$ signaling in in vivo model of maternal diabetes and in vitro embryo culture.

EXAMPLE 7

Maternal Diabetes Results in Alterations of Stress-Activated MAPKS in Yolk Sacs

Oxidative stress generated by maternal hyperglycemia may alter MAPK signaling and leads to aberrant release of cytochrome C and apoptosis. Preliminary experiments were conducted to study potential changes in the levels of phosphorylated MAPKs resulted from maternal hyperglycemia. While there are many MAPKs, the following studies focus on two families, the ERKs (ERK-1 and -2) and JNKs (JNK-1 and -2), for two primary reasons. First, several lines of evidence indicate that ERK and JNK are involved in cell survival and cell death. Second, these factors have also been associated with diabetic complications and with development of embryos and cells under hyperglycemic conditions. These evidences suggest that these MAPKs may be involved in determining cell fates in developing embryos of diabetic mothers. The roles of ERK-1 and -2 and JNK-1 and -2 in diabetic embryopathy, however, have not been extensively studied.

Figure 6A:
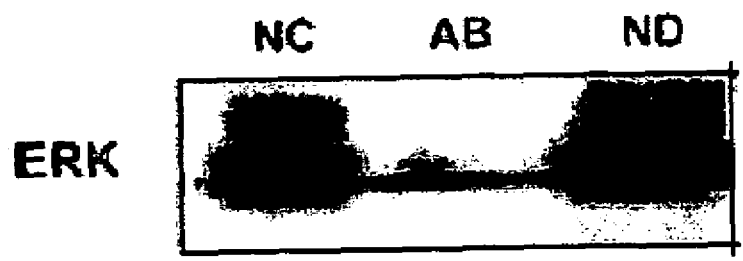
FIGS. 6A-E show Western blots illustrating changes in levels of phosphorylated ERK1/2, JNK1/2 Raf-1 and Akt from yolk sacs.
Figure 6A:
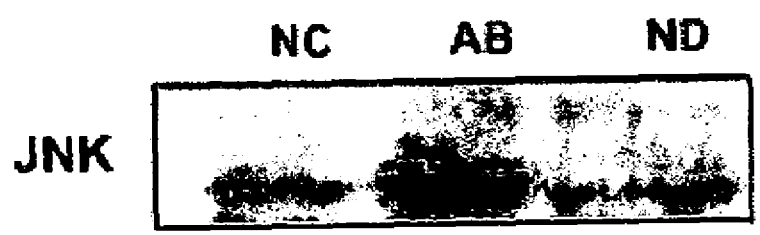
Figure 6A:
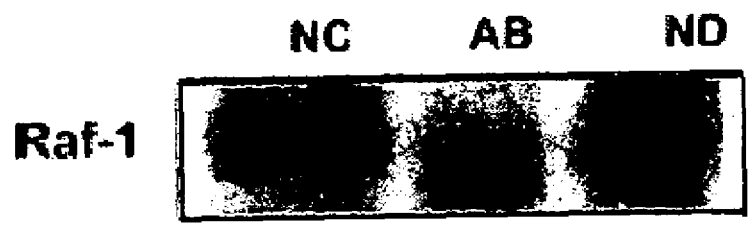
Figure 6A:
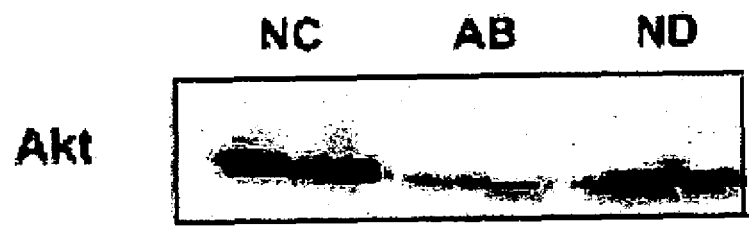
Figure 6B:
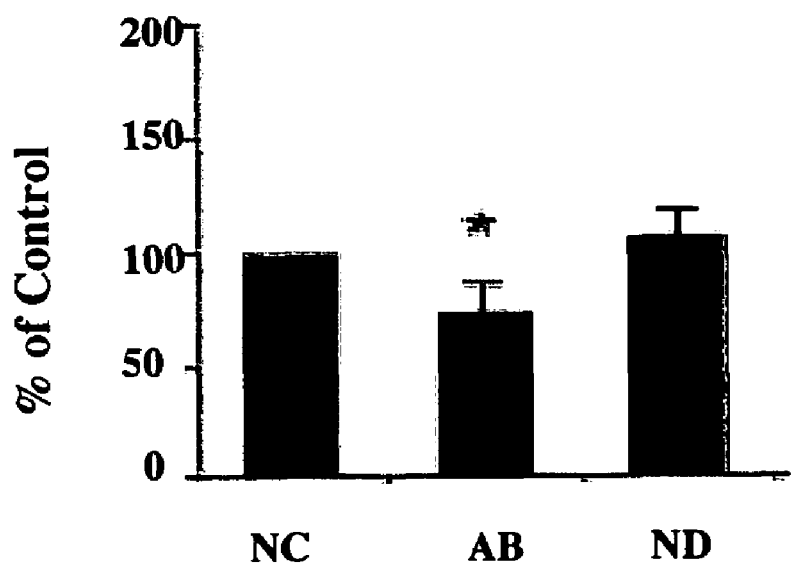
Figure 6C:
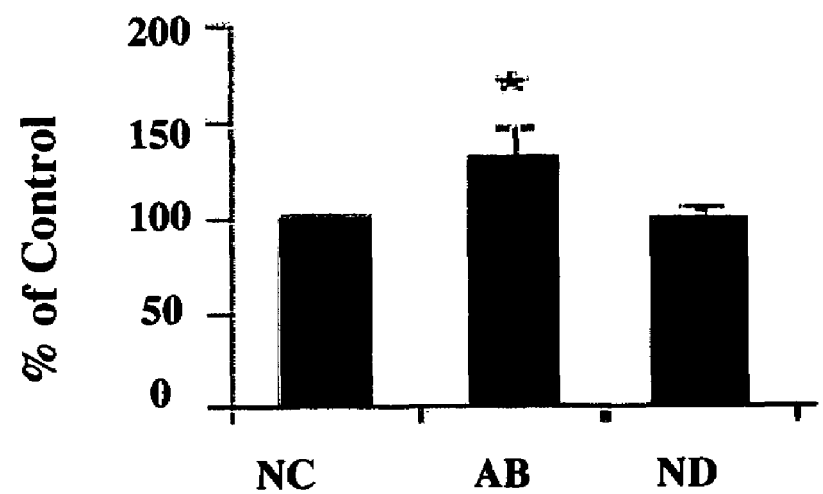
Figure 6D:
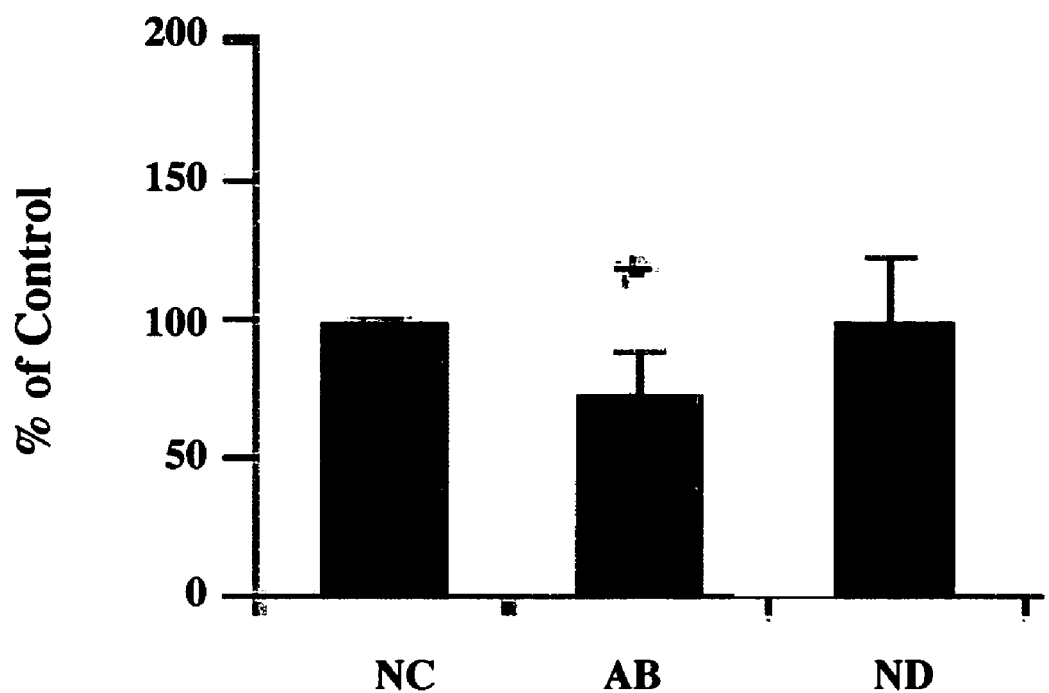
Figure 6E:
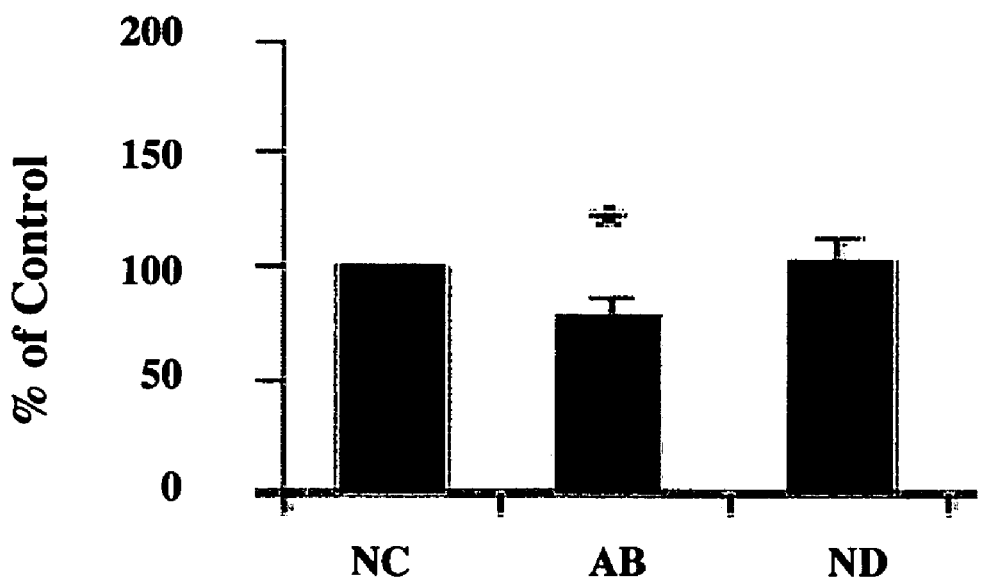

The active forms of ERK and JNK are phosphorylated, so their activation in yolk sac tissues were assessed by Western blot detection of the corresponding phosphoproteins. The levels of phosphorylated Raf-1 which activates ERKs and Akt which is an antiapototic protein were also assessed by western blot. Yolk sac tissues were isolated, protein was extracted and analyzed using Western blotting with antibodies specific for phosphorylated ERK-1 and -2 (p-ERK1/2), JNK-1 and -2 (p-JNK1/2), RAF-1 and Akt (FIG. 6A). Levels of p-ERK1/2, Raf-1 and Akt were dramatically decreased in yolk sac cells of malformed embryos as compared to those of normal embryos from diabetic or non-diabetic mothers (control groups) (FIGS. 6B, 6D and 6F). In contrast, p-JNK1/2 was significantly increased in the yolk sac cells of malformed embryos from diabetic rats as compared to those from the two control groups (FIG. 6C). These findings suggest that maternal diabetes alters activation of ERK and JNK kinases and support the hypothesis that hyperglycemia-induced increases in reactive oxygen species and decreases in antioxidant defense in both the yolk sac and embryo are associated with changes in stress-activated MAPK signaling pathways.

EXAMPLE 8

Antioxidant-Supplemented Diets Decrease Embryo Malformation Rates

It is hypothesized that oxidative stress is the major causative factor for cell membrane injury and developmental abnormalities resulting from diabetic pregnancy. If this hypothesis is correct, it follows that reduction of reactive oxygen species-mediated effects should rescue hyperglycemia-associated birth defects.

To test this hypothesis, from day 1 of pregnancy diabetic and non-diabetic rats were fed with food supplemented daily with safflower oil (a source of arachidonic acid) or vitamin E (an antioxidant source). According to this model, supplementation with arachidonic acid will repair membranes damaged by hyperglycemia-induced increases in reactive oxygen species production, and vitamin E will reduce the damaging effects of oxidative stress.

At E12, embryos were dissected out of uteri and evaluated for neural tube defects (NTDs), which were used as a measure of malformation rates. It was found that dietary supplementation with arachidonic acid or vitamin E reduced the rate of neural tube defects among embryos of diabetic rats (Table 3). The offspring of mothers with unsupplemented diet displayed a malformation rate of 20%, whereas those of mothers with arachidonic acid- or vitamin E-supplemented diets showed malformation rates of only 7.6% and 6.9%, respectively. Importantly, glucose levels remained elevated in the diabetic groups receiving supplementation, demonstrating that the dietary supplements did not prevent hyperglycemia.

These data clearly indicate that in the rat model system, supplementing the diet of diabetic mothers with either arachidonic acid or vitamin E significantly reduced development of neural tube defects despite ongoing hyperglycemia. These results provide important information for developing effective therapeutic strategies to prevent diabetic embryopathy in humans.

TABLE 3

Effects of Arachidonic Acid- or Vitamin E-Supplemented Diet On Neural Tube Defects (NTDs) Rates In Non-Diabetic And Diabetic Rats

| Experimental groups | Embryos (n) | Glucose level (mg/dl) ± SD | NTDs (%) |
|---|---|---|---|
| Non-diabetic | | | |
| Normal diet (unsupplemented) | 163 | 133 ± 22 | 4.8 |
| Normal diet + AA | 97 | 144 ± 24 | 4.1 |
| Normal diet + vitamin E | 153 | 89.2 ± 14 | 5.0 |
| Diabetic | | | |
| Normal diet (unsupplemented) | 280 | 361 ± 48 | 20.0 |
| Normal diet + AA | 162 | 351 ± 48 | 7.6 |
| Normal diet + vitamin E | 154 | 348 ± 59 | 6.9 |

Abbreviations: AA, arachidonic acid (0.5 ml/day); vitamin E, α-tocopherol (400 mg/day)

EXAMPLE 9

Figure 7:
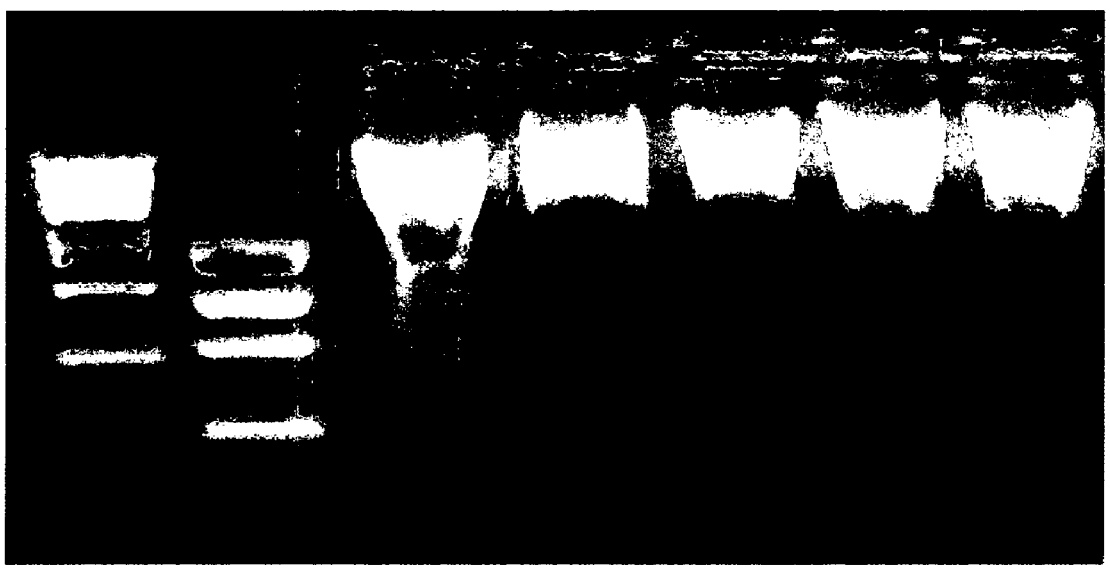
FIG. 7 depicts DNA laddering assay showing the effect of dietary supplementation on apoptosis in yolk sacs. Lanes 1 and 2: DNA size standards; lane 3: malformed embryos of diabetic dams; lane 4: embryos of diabetic dams supplemented with arachidonic acid; lane 5: embryos of diabetic dams supplemented with vitamin E; lane 6; embryos of diabetic dams supplemented with a combination of arachidonic acid, vitamin E and myoinositol lane 7: embryos from non-diabetic dams without supplementation.

Apoptosis is Decreased in Embryonic Yolk Sacs from Mothers with Dietary Supplementation To examine whether supplemented diets affected apoptosis in developing embryos of diabetic dams, DNA fragmentation (an indicator of apoptosis) was analyzed using DNA laddering assays. In yolk sacs of embryos isolated from diabetic mothers whose diets were supplemented with arachidonic acid, vitamin E or a combination of arachidonic acid, vitamin E and myoinositol, DNA fragmentation was eliminated (FIG. 7). These data indicate that antioxidant-supplemented maternal diets prevented apoptosis in embryonic yolk sacs associated with a hyperglycemic environment. This supports the idea that increased apoptosis is related to the process of diabetic embryopathy and is not merely a side-effect of hyperglycemia.

EXAMPLE 10

Effects of Antioxidant Supplementation on MAPK Activity

Figure 8:
FIG. 8 shows the effects of maternal supplementation on the levels of p-ERK1/2, p-JNK1/2, Raf-1 and Akt in embryonic yolk sacs as determined by Western blots analysis. Lane 1: malformed embryos of diabetic dams without supplementation; lane 2: embryos of diabetic dams supplemented with arachidonic acid; lane 3: embryos of diabetic dams supplemented with vitamin E; lane 4: embryos of diabetic dams supplemented with a combination of arachidonic acid, vitamin E and myoinositol; lane 5: normal embryos of non-diabetic dams without supplementation.
Figure 8:
Figure 8:
Figure 8:

To examine how reduction in embryonic malformation rates and apoptosis in yolk sac cells after dietary supplementation with antioxidants correlate with changes in MAPK signaling, diabetic and non-diabetic dams were fed a diet supplemented with arachidonic acid, vitamin E or a combination of arachidonic acid, vitamin E and myoinositol. Levels of phosphorylated ERK1/2, JNK1/2, Raf-1 and Akt in embryonic yolk sac cells were evaluated using Western blot assays. The results presented in FIG. 8 indicate that supplementation with arachidonic acid, vitamin E or a combination of arachidonic acid, vitamin E and myoinositol (Lanes 2 3 and 4 respectively) altered embryo levels of activated ERKs and JNKs from the levels seen in embryos of diabetic dams with unsupplemented diets (Lane 1) to those of non-diabetic rats (Lane 5). These data demonstrate that supplementing the diets of pregnant, diabetic rats with arachidonic acid or vitamin E reverses the status of activation of MAPKs to that seen in embryos of non-diabetic mothers. These results support the hypothesis that during hyperglycemic embryopathy MAPK signaling is altered by oxidative stress, and antioxidant supplementation reverses or prevents this alteration in MAPK activation.

EXAMPLE 11

Determine Critical Developmental Stages at which Nutritional Intervention Exerts Optimal Effects To determine the developmental stage that is necessary for dietary supplementation to be effective as an intervention for diabetic embryopathy, it would be of considerable clinical interest to determine whether the window of development during which organogenesis occurs (E9.5-E12 in the rat) is irreversibly closed at E12 or whether some plasticity remains such that a "bad start" could be rescued or reversed within a prolonged or delayed developmental window if appropriate conditions were restored. These experiments will provide new insights into the regulation of biochemical and molecular events required for normal organogenesis.

One set of pregnant diabetic rats will be allowed to progress in their pregnancy without dietary supplementation until E10.5 (mid-organogenesis), at which time optimal supplementation regimen is initiated to prevent malformations. A second set of mothers will begin the same supplementation regimen on E12 (end of normal organogenesis). Embryos are harvested on E16 and the percents of malformed and normal embryos are assessed using the same methods as described above. A lower malformation rate in supplemented mothers compared to unsupplemented mothers will indicate that supplementation is successful in reversing or rescuing development of malformations. Therefore, this experiment will demonstrate whether supplementation is therapeutically successful when administered during either mid-organogenesis or at the end of organogenesis. These results will also suggest developmental stages critical for targeting prevention of diabetic embryopathy.

What is claimed is:

1. A dietary supplement for reducing birth defects caused by maternal diabetes consisting of:
    (a) an effective amount of lipoic acid;
    (b) an effective amount of vitamin C;
    (c) an effective mount of vitamin E;
    (d) an effective amount of arachidonic acid;
    (e) an effective amount of a folic acid; and
    (f) an effective amount of N-acetylcysteine.

2. The dietary supplement of claim 1, wherein the effective amount of lipoic acid is from about 1 mg to about 100 mg.

3. The dietary supplement of claim 1, wherein the effective amount of vitamin C is from about 10 mg to about 500 mg.

4. The dietary supplement of claim 1, wherein the effective amount of vitamin E is from about 50 IU to about 500 IU.

5. The dietary supplement of claim 1, wherein the effective amount of N-acetylcysteine is from about 250 mg to about 500 mg.

6. The dietary supplement of claim 1, wherein the effective amount of folic acid is from about 100 μg to about 800 μg.

7. The dietary supplement of claim 1, further consisting of an effective amount of myoinositol.

8. A dietary supplement for reducing birth defect caused by maternal diabetes consisting of:
    (a) an effective amount of at least one of lipoic acid, vitamin C and vitamin E;
    (b) an effective amount of arachidonic acid;
    (c) an effective amount of at least one compound that support glutathione synthesis "selected from folic acid and N-acetylcysteine" and; (d) an effective amount of myoinositol.

9. The dietary supplement of claim 8, wherein the effective amount of said lipoic acid is from about 1 mg to about 500 mg.

10. The dietary supplement of claim 8, wherein the effective amount of said vitamin C is from about 10 mg to about 500 mg.

11. The dietary supplement of claim 8, wherein the effective amount of said vitamin E is from about 50 IU to about 500 IU.

12. The dietary supplement of claim 8, wherein the compound that supports glutathione synthesis is methionine/cysteine precursor or a glutathione precursor.

13. The dietary supplement of claim 12, wherein the methionine/cysteine precursor is folic acid and the glutathione precursor is N-acetylcysteine 14. The dietary supplement of claim 13, wherein the effective amount of said folic acid is about 100 μg to about 800 μg and the effective amount of said N-acetylcysteine is from about 250 mg to about 500 mg.

* * * * *